United States Patent [19]

Freiermuth et al.

[11] Patent Number: 5,496,707
[45] Date of Patent: Mar. 5, 1996

[54] ASSAY METHOD FOR HEMICELLULASES USING A COLORED SUBSTRATE

[75] Inventors: Beat Freiermuth; Dieter Werthemann, both of Basle, Switzerland; Alfred Gaertner, San Bruno; Spencer Fisk, Burlingame, both of Calif.

[73] Assignees: Ciba-Geigy Corporation, Tarrytown; Genencor International, Inc., Rochester, both of N.Y.

[21] Appl. No.: 221,649

[22] Filed: Apr. 5, 1994

[51] Int. Cl.$^6$ ............................. C12Q 1/34; C07H 1/00
[52] U.S. Cl. ........................ 435/18; 435/4; 435/14; 435/22; 536/1.11; 536/18.6; 536/102; 536/122; 536/127; 8/473; 8/916; 8/921; 8/930; 8/931; 8/934
[58] Field of Search .................. 435/18.4, 14, 22, 435/305, 311, 315; 536/1.11, 18.6, 102, 122, 127; 8/473, 916, 921, 930, 931, 934

[56] References Cited

U.S. PATENT DOCUMENTS

| | | | |
|---|---|---|---|
| 3,705,149 | 12/1972 | Babson et al. | 435/22 |
| 4,321,364 | 3/1982 | McCleary | 536/18.6 |
| 4,563,421 | 1/1986 | Habenstein | 435/18 |
| 5,199,956 | 4/1993 | Schleuker et al. | 8/473 |
| 5,298,032 | 3/1994 | Schleuker et al. | 8/473 |

OTHER PUBLICATIONS

Ciba Chemical Division, ™Irgazyme 40.
Ciba Chemical Division, ™Pergalase A40.
Magazyme—Product Information Bulletin.
Cole–Parmer 1995–1996 Catalog, p. 352.
E. N. Abrahart, *Dyes and their Intermediates* Pergamon Press, pp. 254–261 (1968).
Carbohydrate Research 67 (1978) 213–222.
Methods of Enzymology 160 (1988) 74–86.

*Primary Examiner*—Michael G. Wityshyn
*Assistant Examiner*—Abdel A. Mohamed
*Attorney, Agent, or Firm*—Kevin T. Mansfield

[57] ABSTRACT

The present invention provides an assay method for hemicellulases comprising a) directly dyeing, using a reactive dye, an insoluble natural product, or a modified form of a natural fibre material; and b) adding the enzyme to the dyed product produced in step a) and, after a specific incubation period, separating the liquid component from the insoluble dyed product, e.g. by a simple filtration, and determining the amount of dyestuff liberated in the the separated solution by spectrophotometric means. A combined mixing and dispensing device for use in the method of the present invention is also provided.

13 Claims, No Drawings

ASSAY METHOD FOR HEMICELLULASES USING A COLORED SUBSTRATE

The present invention relates to an assay method for hemicellulases using a colored substrate and to a combined mixing and dispensing device for use in the method of the present invention.

Various assay methods are known for hemicellulases using a coloured substrate. These known methods involve producing a colored substrate and carrying out the assay using the substrate.

For conventional chromogenic substrates for use in the determination of the enzyme activity of hemicellulases such as xylanase, mannanase or galactosidase, the uncolored substrate is fast produced from a natural product by means of extraction. This substrate is then reacted with a reactive dyestuff in alkaline solution. Finally, the colored substrate so obtained is freed from unfixed dyestuff by dialysis or by repeated precipitation and washing with organic solvent.

Known steps for determining the enzyme activity involve adding the enzyme, dissolved in a solvent, to the chromogenic substrate and, after a specific incubation period, adding further solvent. The liquid component is separated from the insoluble substrate by filtration or by centrifugation and the amount of dyestuff liberated, in the tiltrate or the supernatant solution, is determined. The enzymatic activity is then proportional to the measured absorption value of the solution.

This type of process is described, e.g., in U.S. Pat. No. 4,321,364 and in the articles by B. McCleary in *Carbohydrate Research* 67 (1978) 213–222 and in *Methods of Enzymology* 160, (1988) 74–86.

In EP-A-0 034 692, a process is described for the production of indicator papers for the semi-quantitative detection of endohydrolases. A reactive dyestuff or other detection group is chemically bonded to a carbohydrate, preferably a glucose polymer such as starch. Once again, it is necessary to wash away unfixed dyestuff using methanol.

The colored carbohydrate so obtained, together with a buffer solution, is dried on to paper to produce bleed-free indicator paper. The dyestuff is liberated when an amylase-containing sample is dropped on to the paper. The amylase is detected by the migration of the dyestuff into undyed zones of the paper or, after washing, by a local bleaching where the enzyme was present. This method, however, suffers from the disadvantage that it provides only a semi-quantitative detection.

A new assay method for hemicellulases using a colored substrate is now provided which does not require an extraction step for the production of the substrate and which does not require an expensive washing operation after the dyeing process.

Accordingly, the present invention provides an assay method for hemicellulases comprising a) directly dyeing, using a reactive dye, an insoluble natural product, or a modified form of a natural fibre material; and b) adding the enzyme to the dyed product produced in step a) and, after a specific incubation period, separating the liquid component from the insoluble dyed product, e.g. by a simple filtration, and determining the amount of dyestuff liberated in the the separated solution by spectrophotometric means.

Hemicellulases which may be assayed according to the method of the present invention include, e.g., xylanase, mannanase and galactosidase.

The insoluble natural product dyed in step a) of the method according to the present invention may be wood or other vegetable material that has been mechanically decomposed or homogenised. Preferred are wood or other vegetable material that has been subjected to a chemical hydrolysis, such as the sulphate or sulphite process, with or without bleaching with bleach chemicals such as oxygen, ozone, peroxide, chlorine-containing or chlorine-generating compounds or reducing materials.

The reactive dyestuff used in step a) may contain any leaving group, in particular a halogen atom, which can undergo nucleophilic displacement by a hydroxyl group of the hemicellulose, or may contain an activated ethylene bond which can add to a hydroxyl group of the hemicellulose. Examples of such reactive dyestuffs include those containing one or more reactive groups selected from an s-triazine group, in particular a 2,4-dichloro-s-triazinylamino group or a monochloro- or monofluoro-s-triazinylamino group; a 2-chlorobenzothiazole group; a 2,3-dichloroquinoxaline group; a dichloropyridazone group; a dichloropyrimidinylamino group; a trichloro-, dichlorofluoro- or difluorochloro-pyrimidinylamino group; a beta-sulfatoethyl sulfone group; a beta-sulfatoethylamide of a sulfonic acid; a beta-chloroethyl sulfone group; or a vinyl sulfone group.

The reactive dyestuff used in step a) is preferably a bi-reactive dyestuff, since these dyes provide a particularly high fixing rate.

The dyeing conditions applied in step a) are preferably those used for dyeing with reactive dyes, the use of a dyeing temperature ranging from 10° to 40° C. and a pH range of 10 to 11, being preferred.

Further details of these reactive dyestuffs and the conditions used during their application may be found in "The Chemistry of Synthetic Dyes", vol. VI, Reactive Dyes, edited by K. Venkataraman, 1972 (Academic Press).

In the assay step b), the temperature should be maintained within the activation range of the enzyme, that is within the range of from about 0° to 100° C. Preferably, the pH is held in the vicinity of the pH optimum of the particular hemicellulase enzyme under test. The incubation time preferably ranges from 2 minutes to 4 hours, more preferably from 30 minutes to 60 minutes.

When carrying out a large number of determinations, it is advantageous to operate the method according to the present invention using a soluble substrate, since it is easier to automatise volumetric dosing than to conduct weighing operations.

The method according to the present invention has the following advantages relative to known methods:

i) when carrying out the assay step b), no solvent is necessary in order to precipitate unreacted substrate after the incubation; a simple filtration suffices for the separation of the liquid and substrate; and the dyestuff-containing solution can be directly measured by spectrophotometric means (the liberated amount of dye is proportional to the enzyme concentration in the absorbance range of 0–2, preferably 0.2–1.1);

ii) the method according to the present invention is significantly superior to known methods when a rapid test for aqueous solutions containing hemicellulases or mixtures of hemicellulases with cellulases is to be conducted; and iii) when mixtures of enzymes are being examined, any synergistic action of the various enzymes on the natural substrate can be evaluated.

The present invention also provides a combined mixing and dispensing device for use in the method of the present invention. The device comprises a chamber adapted to receive an enzyme solution and a dyed product, and adapted to discharge a liquid while retaining any solid in the chamber; agitator means for agitating the enzyme and the dyed product; and pump means adapted to draw a sample of the enzyme solution into the chamber and, after the agitation of the enzyme and the dyed product, to discharge liquid from the chamber.

Preferably, the chamber is cylindrical in form, is produced from a transparent plastics material and is graduated so that respective amounts of liquid drawn into the chamber and discharged therefrom can be determined visually. Preferably, the agitator means is a solid sphere enabling agitation of the enzyme and the dyed product to be effected by manual shaking of the charged chamber. In its simplest and preferred form, the pump means is a manually movable cylindrical flange adapted to form a sliding fit within the cylindrical chamber.

In operation, an enzyme solution is drawn into the chamber which contains the dyed product and the agitator means. The contents of the chamber are agitated. After incubation, a portion of the liquid in the chamber is discharged and its optical density determined.

The following Examples further illustrate the present invention.

EXAMPLE 1

A) Fibres of unbleached bamboo kraft pulp (5 g. dry weight) are treated at a consistency of 2.5% with 500 mg. of a commercial form of Reactive Red 238. The suspension is stirred and, after 5 minutes, 20 g. of sodium sulphate are added.

After 45 minutes, 9 g. of anhydrous soda are added, as an aqueous solution, to assist in fixing the dye. After a further 2 hours, the dyed cellulose is separated from the liquor on a suction filter, dispersed twice for 30 minutes in 150 mls of fresh water at 60° C., filtered and stored at a consistency of 1% over 16 hours in cold water before again being filtered. Water is added to give a total volume of 100 mls and the pulp suspension is homogenised using a blender mixing device. The suspension is then shock-frozen and freeze dried, B) To 40 mg of the pulp from A) in an Eppendorf tube, there are added 1.25 mls of an 0.07 mol/l phosphate buffer solution having a pH of 6. 100 µl of xylanase enzyme solution in phosphate buffer are then added. The enzyme solution contains 2 µl of a commercial form of xylanase (IRGAZYME 40-X4Ciba-Geigy Corp., Chemicals Division, Greensboro, N.C. 27419) per ml of solution. The sample is shaken vigorously and incubated at 30° C. After 30 minutes, about 1 ml of the solution is withdrawn using a pipette having a built-in filter. The sample is placed in a 1 cm cuvette and has an optical density of 0.395 at 545 nm When measured in an absorption spectrophotometer.

EXAMPLE 2

A) Fibres of bleached mechanical wood pulp (5 g dry weight) are dyed and freeze dried in the manner described in Example 1 A ).

B) To 40 mg of the pulp from A) in an Eppendorf tube, there are added 1.25 mls of an 0.07 mol/l phosphate buffer solution having a pH of 6. 100 µl of mannanase enzyme solution in phosphate buffer are then added. The enzyme solution contains 250 µl of a commercial form of mannanase (Megazyme β-Mannanase Megazyme Pty. Ltd., Warriewood (Sydney) N.S.W., 2102, Austrailia) per ml of solution.

The sample is shaken vigorously and incubated at 30° C. After 30 minutes, about 1 ml of the solution is withdrawn using a pipette having a built-in filter. The sample is placed in a 1 cm cuvette and has an optical density of 0.313 at 545 nm when measured in an absorption spectrophotometer.

EXAMPLE 3

A) Fresh, oxygen-delignified, unbleached eucalyptus sulphate pulp (5 g dry weight) are dyed and freeze dried in the manner described in Example 1 A).

B) To 40 mg of the pulp from A) in an Eppendorf tube, there are added 1.25 mls of an 0.07 mol/l phosphate buffer solution having a pH of 6. 100 µl of enzyme solution in phosphate buffer are then added. The enzyme solution contains 10 gl of a commercial form of cellulases/hemicellulases (PERGALASE A40Ciba-Geigy Corp., Chemicals Division, Greensboro, N.C. 27419) per ml of solution.

The sample is shaken vigorously and incubated at 50° C. After 60 minutes, about 1 ml of the solution is withdrawn using a pipette having a built-in filter. The sample is placed in a 1 cm cuvette and has an optical density of 1.017 at 545 nm when measured in an absorption spectrophotometer.

We claim:

1. In an assay method for hemicellulases having the steps of a) dyeing, using a reactive dye, wood or other vegetable material that has been mechanically decomposed or homogenized; and b) adding an enzyme to the dyed material produced in step a) and, after an incubation period of from 2 minutes to 4 hours, separating a liquid component from the dyed material and determining the amount of dye liberated in the separated liquid component by spectrophotometric means, the improvement comprising dyeing insoluble wood or other vegetable material that has been mechanically decomposed or homogenized in step a) and, in step b), after incubation, separating the liquid component from the dyed material without the use of an organic solvent.

2. A method according to claim 1 in which the liquid component is separated from the insoluble dyed material by a simple filtration.

3. A method according to claim 1 in which the hemicellulase assayed is xylanase, mannanase or galactosidase.

4. A method according to claim 1 in which the insoluble wood or other vegetable material has been subjected to chemical hydrolysis.

5. A method according to claim 4 in which the chemical hydrolysis is effected by the sulphate or sulphite process.

6. A method according to claim 5 in which the chemical hydrolysis is effected in the presence of bleach chemicals selected from the group consisting of oxygen, ozone, peroxide, and chlorine-containing or chlorine-generating compounds.

7. A method according to claim 1 in which the reactive dye used in step a) contains a leaving group which can undergo nucleophilic displacement by a hydroxyl group of a hemicellulose, or contains an activated ethylene bond which can add to a hydroxyl group of a hemicellulose.

8. A method according to claim 7 in which the leaving group is a chlorine atom.

9. A method according to claim 7 in which the reactive dye is one containing one or more reactive groups selected from the group consisting of an s-triazine group; a 2-chlorobenzothiazole group; a 2,3-dichloroquinoxaline group; a dichloropyridazone group; a dichloropyrimidinylamino group; a trichloro-, dichlorofluoro- or difluorochloro-pyrimidinylamino group; a beta-sulfatoethyl sulfone group; a beta-sulfatoethylamide of a sulfonic acid; a beta-chloroethyl sulfone group; and a vinyl sulfone group.

10. A method according to claim 9 in which the s-triazine group is a 2,4-dichloro-s-triazinylamino group or a monochloro- or monofluoro-s-triazinylamino group.

11. A method according to claim 7 in which the reactive dye is a bi-reactive dye.

12. A method according to claim 1 in which, in step b), the temperature is maintained within a range of from 0° to 100° C. during the incubation period.

13. A method according to claim 1 in which the incubation time is from 30 minutes to 60 minutes.

\* \* \* \* \*